US008278406B2

(12) United States Patent
Masters et al.

(10) Patent No.: US 8,278,406 B2
(45) Date of Patent: Oct. 2, 2012

(54) BIOACTIVE AND BIOCOMPATIBLE POLYURETHANE-BUTHANEDIOL-GLYCOSAMINOGLYCAN SALT COPOLYMERS

(75) Inventors: Kristyn S. Masters, Madison, WI (US); Wendy C. Crone, Madison, WI (US); Fangmin Xu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 71 days.

(21) Appl. No.: 12/110,096

(22) Filed: Apr. 25, 2008

(65) Prior Publication Data

US 2008/0293906 A1 Nov. 27, 2008

Related U.S. Application Data

(60) Provisional application No. 60/926,449, filed on Apr. 27, 2007, provisional application No. 60/926,979, filed on Apr. 27, 2007.

(51) Int. Cl.
*C08G 18/00* (2006.01)
(52) U.S. Cl. ........................... 527/300; 527/301
(58) Field of Classification Search .................. 527/300, 527/301
See application file for complete search history.

(56) References Cited

U.S. PATENT DOCUMENTS

| | | | |
|---|---|---|---|
| 4,500,676 A | 2/1985 | Balazs et al. | |
| 5,202,431 A | 4/1993 | della Valle et al. | |
| 5,342,348 A | 8/1994 | Kaplan | |
| 5,545,213 A * | 8/1996 | Keogh et al. ..................... | 600/36 |
| 6,107,416 A | 8/2000 | Patnaik et al. | |
| 6,197,051 B1 | 3/2001 | Zhong | |
| 6,335,384 B1 | 1/2002 | Evans et al. | |
| 6,346,117 B1 | 2/2002 | Greenhalgh | |
| 6,364,823 B1 | 4/2002 | Garibaldi et al. | |
| 6,579,978 B1 | 6/2003 | Renier et al. | |
| 7,045,585 B2 * | 5/2006 | Berry et al. ..................... | 527/300 |
| 7,201,918 B2 | 4/2007 | Cruise | |
| 2002/0165572 A1 | 11/2002 | Saadat | |
| 2003/0225391 A1 | 12/2003 | Cragg et al. | |
| 2004/0102805 A1 | 5/2004 | Cheng et al. | |
| 2004/0110722 A1 | 6/2004 | Ornberg et al. | |
| 2004/0225279 A1 | 11/2004 | Raymond | |
| 2005/0158272 A1 | 7/2005 | Whirley et al. | |
| 2005/0238716 A1 * | 10/2005 | Verrijk et al. ..................... | 424/469 |
| 2005/0267510 A1 | 12/2005 | Razack | |
| 2006/0089710 A1 | 4/2006 | Ornberg et al. | |

FOREIGN PATENT DOCUMENTS

| | | |
|---|---|---|
| EP | 0184465 A | 6/1986 |
| EP | 0184465 A2 | 6/1986 |
| WO | 98/45335 A1 | 10/1998 |
| WO | WO9845335 A | 10/1998 |
| WO | 0128434 A1 | 4/2001 |
| WO | 2004039422 A1 | 5/2004 |
| WO | 2006000763 A2 | 1/2006 |
| WO | 2007016251 A2 | 2/2007 |

OTHER PUBLICATIONS

Broderick, JP, et al., "Intracerebral hemorrhage more than twice as common as subarachnoid hemorrhage," J Neurosurg., vol. 78, p. 188-191, Feb. 1993.
Cognard, C., et al., "Long-term Angiographic Follow-up of 169 Intracranial Berry Aneurysms Occluded with Detachable Coils," Radiology, vol. 212, No. 2, pp. 348-356, Aug. 1999.
Duerig, T.W., et al., "Superelastic Nitinol for Medical Devices," Medical Plastics and Biomaterials Magazine, 1997, pp. 30-43.
Freiherr, G., "The Light Stuff: Optical Imaging in Medical Diagnosis," Medical Device and Diagnostic Industry Magazine, Jun. 1998, pp. 52-59.
Kuo and Ma, "Ionically crosslinked alginate hydrogels as scaffolds for tissue engineering: Part 1. Structure, gelation rate and mechanical properties," Biomaterials, 2001, vol. 22, pp. 511-521.
Leach, JB, et al., "Hyaluronan" in Encyclopedia of Biomaterials and Biomedical Engineering, Wnek Ge, et al., eds., Marcel Dekker, New York, 2004, pp. 779-789.
Linhardt, RJ, et al., "Isolation and characterization of human heparin," Biochemistry, 1992, vol. 31(49), pp. 12441-12445.
Otsuka and Wayman, eds., "Shape Memory Materials," Cambridge University Press, 1998, pp. 49-96, 133-143, and 267-281.
Schmitz-Rode, T., et al., "Embolotherapy of Aneurysms Under Temporary Balloon Occlusion of the Neck, In Vitro Study of a Newly Designed Eccentric Balloon Catheter," Investigative Radiology, 1999, vol. 34(4), pp. 317-321.
Shabalovskaya, SA, "Biological Aspects of TiNi Alloy Surfaces," Journal de Physique IV, 1995, C8-1199.
Tiwari, A., et al., "New prostheses for use in bypass grafts with special emphasis on polyurethanes," Cardiovascular Surgery (London, England), vol. 10, No. 3, pp. 191-197 (2002).
Xu, et al., "The haemocompatibility of polyurethane-hyaluronic acid copolymers," Biomaterials, vol. 29, p. 150-160, 2008.
International Search Report and Written Opinion for PCT/US2008/061492 mailed Jul. 24, 2008.
Kwan, Kwon, and Borden, "Successful Thrombolysis in the Vertebrobasilar Artery after Endovascular Occlusion of a Recently Ruptured Large Basilar Tip Aneurysm," Apr. 16, 1995, pp. 847-851.
International Search Report and Written Opinion for PCT/US2008/061503 mailed Jun. 29, 2009.
Invitation to Pay Additional Fees from PCT/US2008/061503, dated Apr. 16, 2009.
"Mixture," http://dictionary.reference.com/browse/mixture, printed Jul. 26, 2010.
Official Letter from the European Patent Office dated Jan. 25, 2012.

\* cited by examiner

*Primary Examiner* — Edward Cain
(74) *Attorney, Agent, or Firm* — Armstrong Teasdale LLP (57) ABSTRACT

A bioactive and biocompatible polyurethane-butanediol-glycosaminoglycan copolymer for use in medical implant devices. The biocompatible urethane component being the reaction product of 4,4'-methylene-di-(p-phenyl isocyanate) and poly(tetramethylene oxide)n and further reacted with 1,4-butanediol, wherein n=10 to 40. The bioactive glycosaminoglycan being a salt of hyaluronic acid, such as a cetylpyridinium salt acid having 5 to 10,000 repeating units or a salt of heparin, such as a dimethyldioctadecylammonium salt of heparin has 5 to 65 repeating units or a suitable salt of dermatan sulfate. The weight content of the bioactive glycosaminoglycan is an amount sufficient to render the copolymer bioactive. The copolymers described herein have excellent hemocompatibility and biocompatibility.

24 Claims, 12 Drawing Sheets

BIOACTIVE AND BIOCOMPATIBLE POLYURETHANE-BUTHANEDIOL-GLYCOSAMINOGLYCAN SALT COPOLYMERS

CROSS REFERENCE TO RELATED APPLICATIONS

This patent application claims priority to U.S. Provisional Patent Application Ser. Nos. 60/926,449 and 60/926,979, both of which were filed on Apr. 27, 2007, the entirety of each is hereby incorporated by reference.

STATEMENT REGARDING FEDERALLY SPONSORED RESEARCH OR DEVELOPMENT

This invention was made with United States government support awarded by the following agencies:
NIH EB005440
NSF 0134385
USAF/AFOSR FA9550-04-1-0109
The United States government has certain rights in this invention.

BACKGROUND OF THE INVENTION

Polyurethane copolymers have been widely used for numerous biomedical applications due to their excellent mechanical properties, biocompatibility, and hemocompatibility. In contrast to other materials used in vascular applications, such as polytetrafluoroethylene (PTFE) and polyethylene terephthalate (PET), polyurethane-based materials support the growth of endothelial cells and possess mechanical properties that match the native vasculature. (Tiwari A et al., *Cardiovascular surgery* (London, England) 10, 191 (2002).

Surface and/or bulk modification of polyurethane may be accomplished, such as by attaching biologically active species to reactive groups on the polyurethane molecule. Such modifications may be designed to control/mediate host wound healing responses. However, polyurethane is not inherently bioactive.

Hyaluronic acid (HA) and heparin are glycosaminoglycans (GAGs) found in all mammals. Hyaluronic acid is a unique and highly versatile biopolymer. Hyaluronic acid plays a vital role in embryonic development, extracellular matrix homeostasis, wound healing, and tissue regeneration. However, the exact mechanisms of hyaluronic acid's regulation of these events are unknown. The behavior and cell influences of hyaluronic acid are highly dependent upon its concentration and molecular weight. Biomaterials made from derivatized and cross-linked hyaluronic acid have been reported in the bioengineering community for applications such as orthopedic, cardiovascular, ophthalmology, dermatology, and general applications in tissue engineering, surgery and drug delivery. Hyaluronic acid is naturally derived and nonimmunogenic. It also has multiple sites for modification and inherent biological activities. (Leach J B et al., *Encyclopedia of Biomaterials and Biomedical Engineering* 2004, p. 779).

BRIEF DESCRIPTION OF THE INVENTION

One aspect of the invention is a copolymer comprising the reaction product of a biocompatible urethane and a bioactive polysaccharide. "Bioactive" refers to molecules that actively participate in events related to native biological regulation or function, such as molecules that inhibit platelet adhesion and/or support appropriate cellular activity. "Biocompatible" refers to molecules that provide structural and mechanical properties in physiological environments without eliciting any material undesirable effects in cells or without inducing any material undesirable local or systemic responses in the host, such as uncontrolled activation of immunogenic or thrombotic cascades. The weight content of the cetylpyridinium salt of hyaluronic acid is an amount sufficient to render the copolymer bioactive. Preferably, the weight content of the polyurethane-diol is an amount sufficient to render the copolymer sufficiently flexible and rigid for endovascular delivery into a vascular aneurysm and for use as a polymeric shell, having coiled NiTi wire disposed therein, within the vascular aneurysm.

In an exemplary embodiment of the copolymer, the bioactive polysaccharide is a bioactive glycosaminoglycan, which includes glycosaminoglycan salts.

Figure 1:
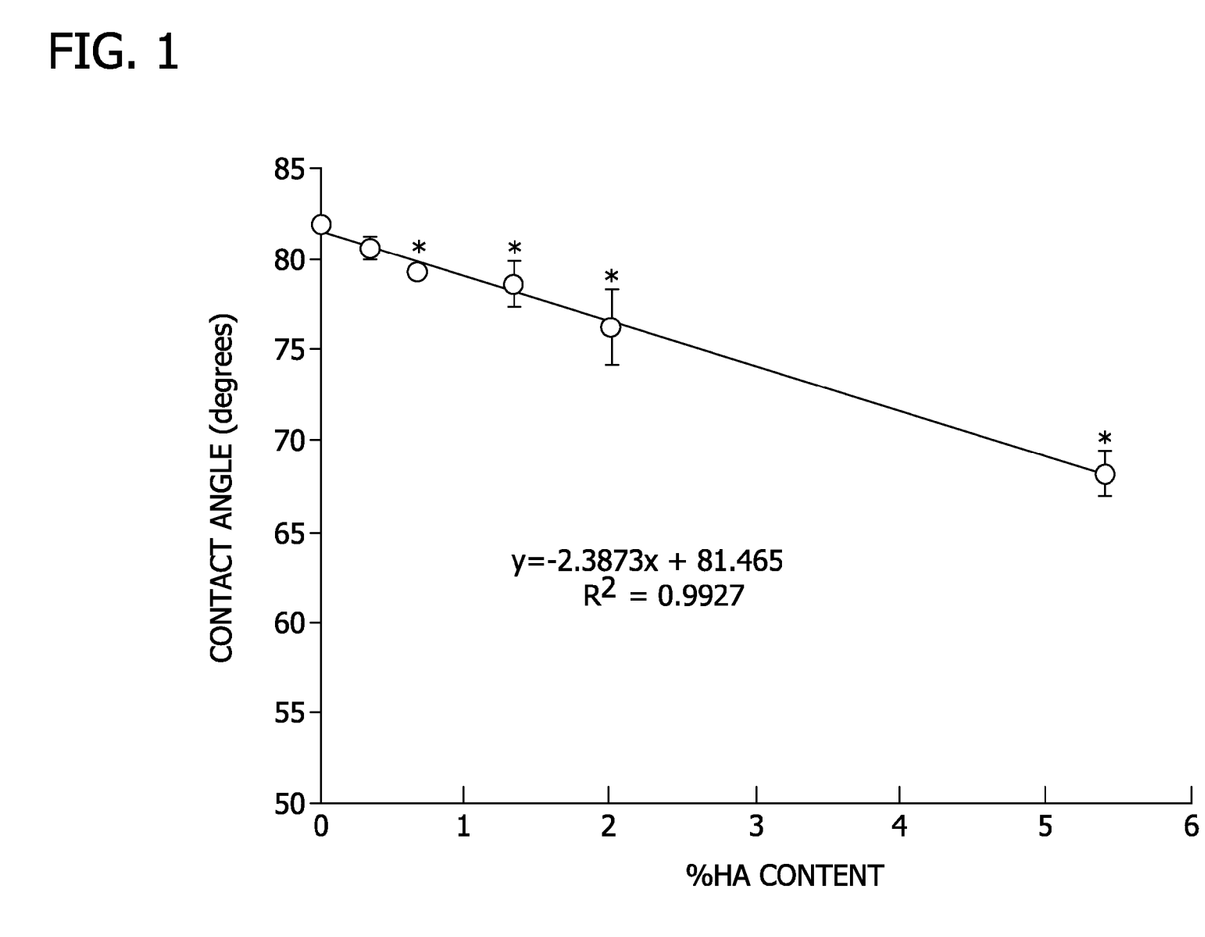
FIG. 1 is a line graph illustrating the contact angle of diH$_2$O on PUBD-HA copolymer films of varying hyaluronic acid content, whereby hydrophilicity increases with increasing hyaluronic acid content, and whereby the control 1,4-butanediol polyurethane (PUBD) polymer is shown.
Figure 2:
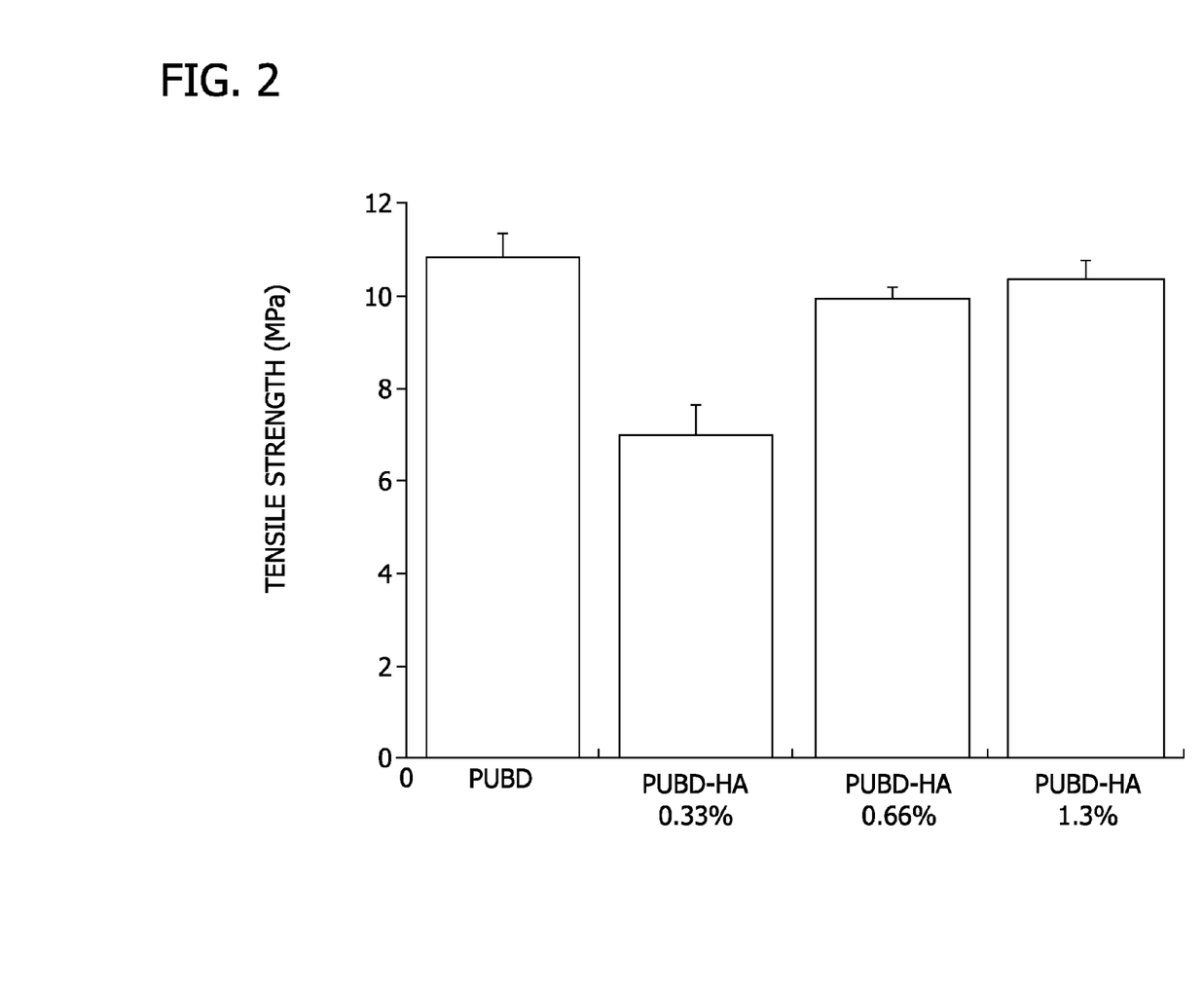
FIG. 2 is a bar graph illustrating tensile strength of PUBD-HA copolymer films of varying hyaluronic acid content compared to the PUBD control.
Figure 3:
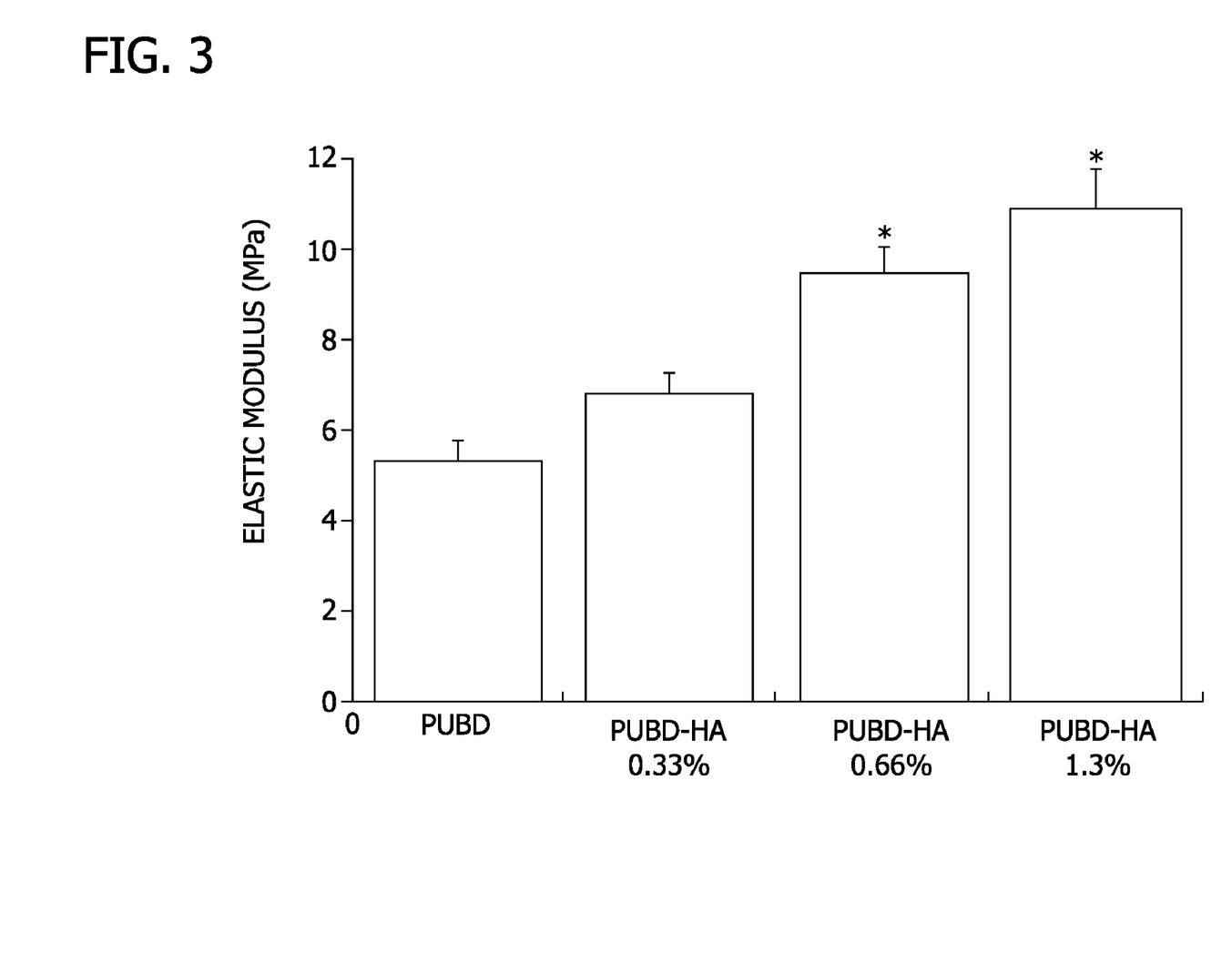
FIG. 3 is a bar graph illustrating elastic modulus of PUBD-HA copolymer films of varying hyaluronic acid content compared to the PUBD control.
Figure 4:
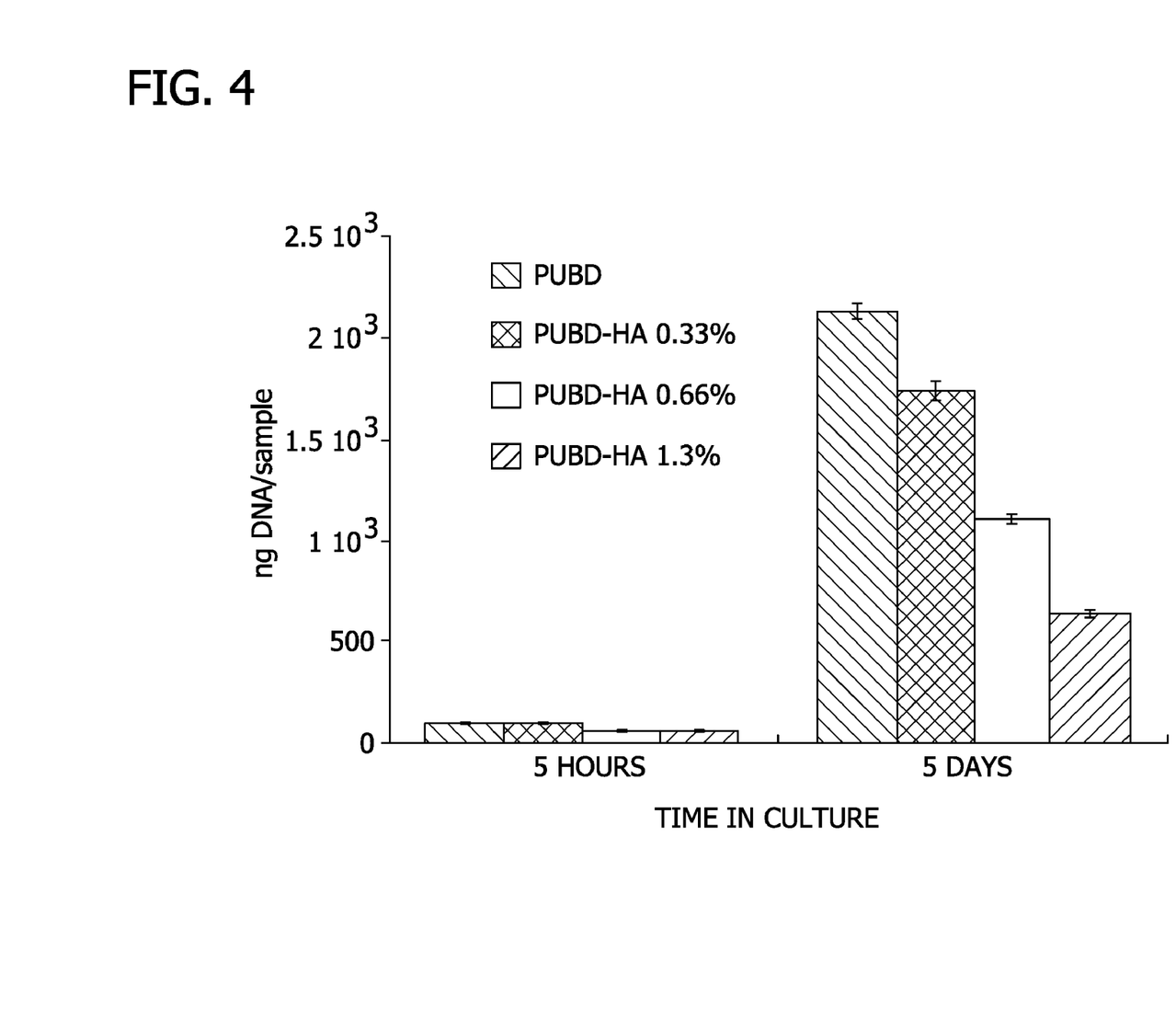
FIG. 4 is a bar graph illustrating fibroblast adhesion and proliferation on PUBD-HA copolymer films of varying hyaluronic acid content compared to the PUBD control.
Figure 5:
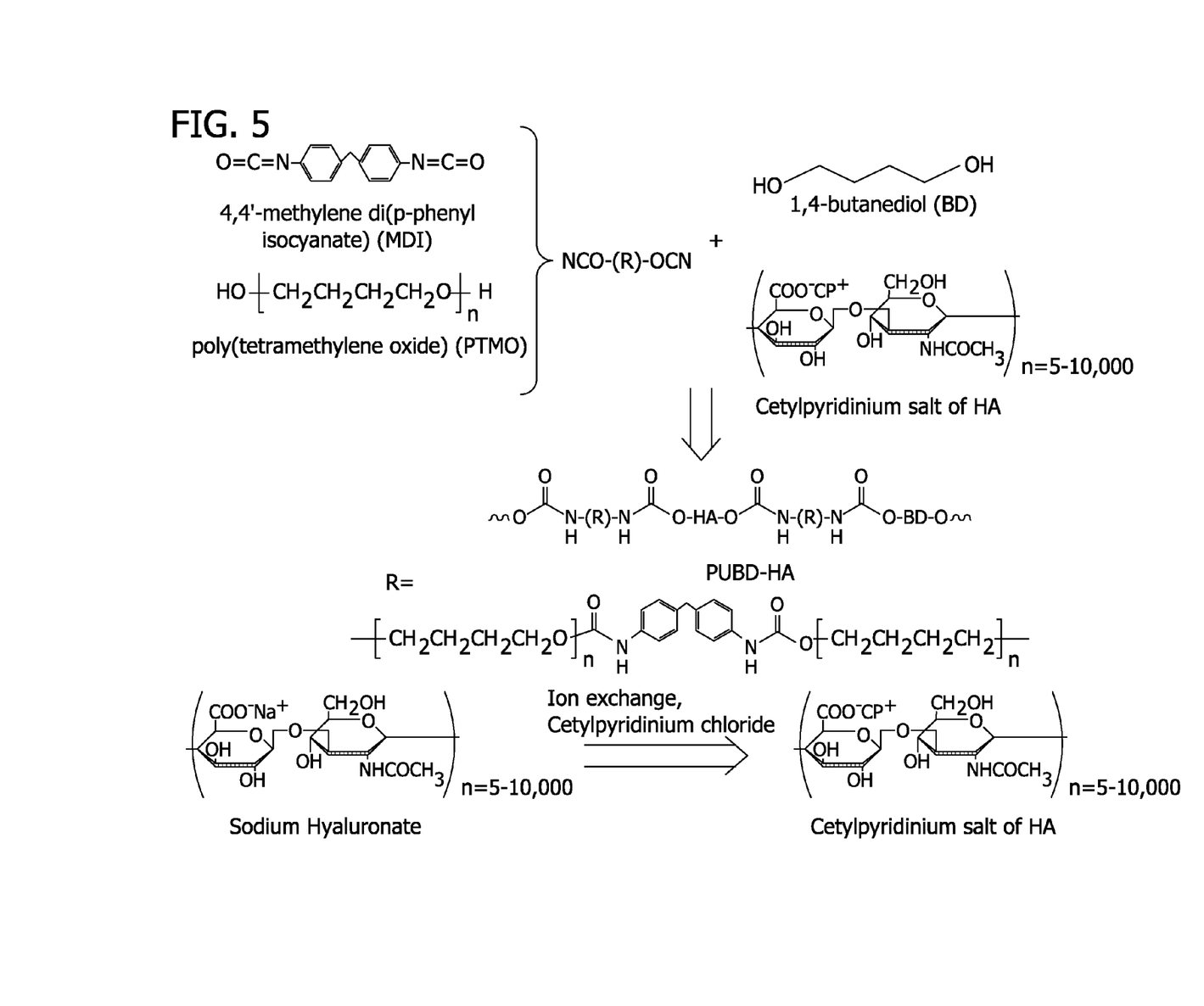
FIG. 5 shows the synthesis of the PUBD-HA copolymer and synthesis of DMF-soluble HA salt.
Figure 6:
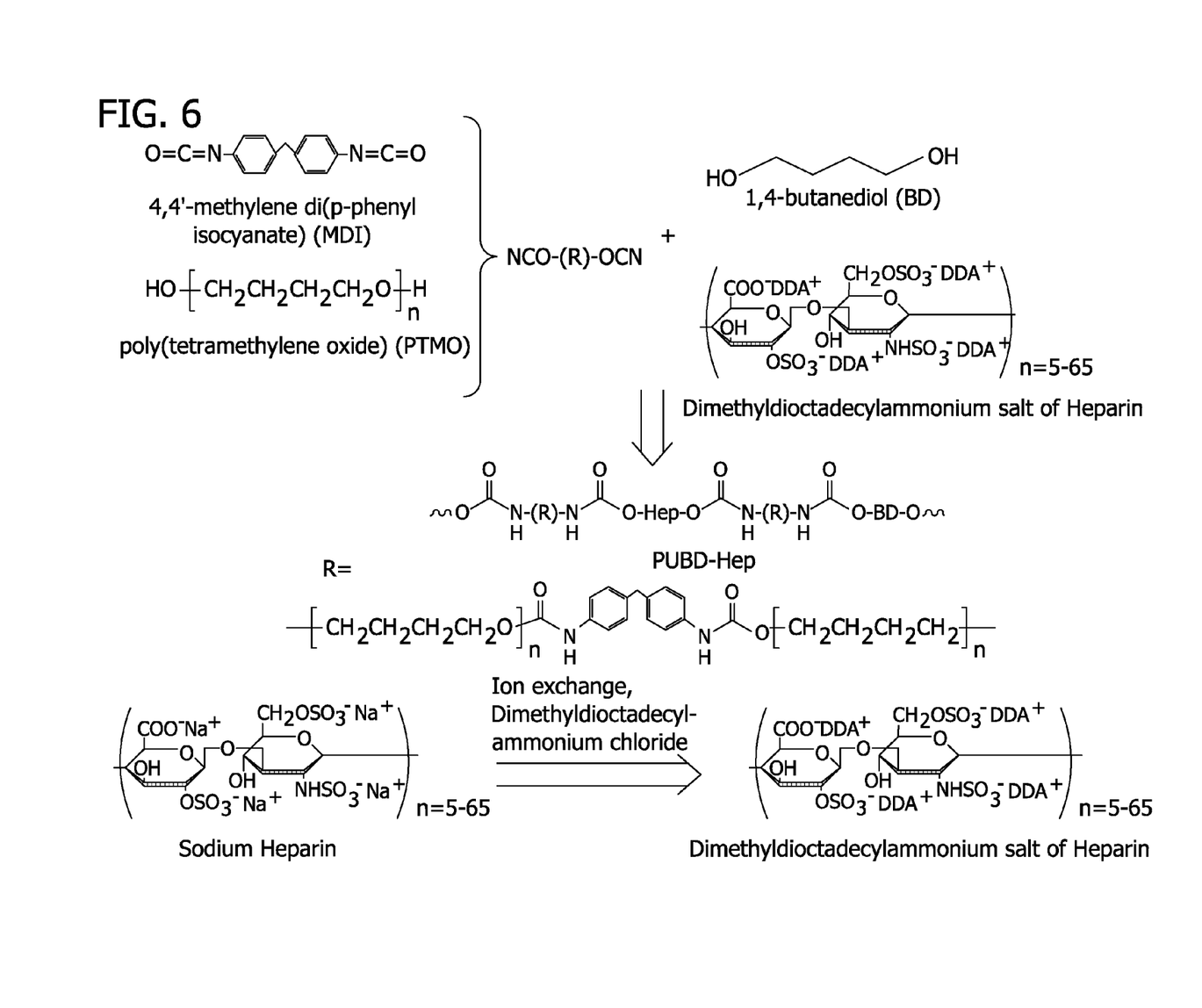
FIG. 6 shows the synthesis of PUBD-heparin copolymer and synthesis of DMF-soluble heparin salt.

In another exemplary embodiment of the copolymer, the bioactive glycosaminoglycan is a suitable salt of hyaluronic acid or a suitable salt of heparin, which includes such salts that are sufficiently soluble in dimethylformamide (DMF) or tetrahydrofuran (THF) to react with the other reactants as set forth in the chemical synthesis at FIGS. 5 and 6 and provide the copolymer end-product.

In another exemplary embodiment of the copolymer, the bioactive glycosaminoglycan is a suitable salt of hyaluronic acid or a suitable salt of heparin, or a suitable salt of dermatan sulfate, which includes such salts that are sufficiently soluble in dimethylformamide (DMF) or tetrahydrofuran (THF) to react with the other reactants as set forth in the chemical synthesis at FIGS. 5 and 6 and provide the copolymer end-product.

In another exemplary embodiment of the copolymer, the salt of hyaluronic acid is a cetylpyridinium salt or a tetrabutylammonium salt, and the salt of heparin is a dimethyldioctadecylammonium salt.

In another exemplary embodiment of the copolymer, the salt of hyaluronic acid is the cetylpyridinium salt.

In another exemplary embodiment of the copolymer, the salt of hyaluronic acid has 5 to 10,000 repeating units, and the dimethyldioctadecylammonium salt of heparin has 5 to 65 repeating units.

In another exemplary embodiment of the copolymer, the biocompatible urethane is the reaction product of 4,4'-methylene-di-(p-phenyl isocyanate) and poly(tetramethylene oxide)$_n$, which is then further reacted with 1,4-butanediol. Preferably, n=10 to 40.

In another exemplary embodiment of the copolymer, the biocompatible urethane is the reaction product of a suitable isocyanate-containing molecule and a suitable poly($C_{2-10}$ alkylene oxide)$_n$ which is further reacted with a suitable $C_{4-50}$ diol-containing molecule. Preferably, n=10 to 40. Such suitable isocyanate-containing molecules, poly($C_{2-10}$ alkylene oxide)$_n$ molecules, and the $C_{4-50}$ diol-containing molecules are sufficiently soluble in DMF or THF to react and provide the end product copolymer as set forth in FIGS. 5 and 6.

The $C_{2-10}$ alkylene group in the poly($C_{2-10}$ alkylene oxide)$_n$ molecule may be linear or branched, substituted or un-substituted. The $C_{4-50}$ group in the diol-containing molecule may also be linear or branched, substituted or un-substituted.

In another exemplary embodiment of the copolymer, the weight content of the bioactive polysaccharide, glycosaminoglycan, suitable salt of hyaluronic acid or suitable salt of heparin is in the range of about 0.05% to about 30%.

In another exemplary embodiment of the copolymer, the high and/or low endpoints of the weight content of the bioactive polysaccharide, glycosaminoglycan, suitable salt of hyaluronic acid or suitable salt of heparin include any combination of about 0.05%, 0.1%, 0.33%, 0.66%, 1.3%, 2.0%, 5.4%, 10%, 20% and 30%.

Another aspect of the invention is a method of making a bioactive and biocompatible polyurethane-diol-polysaccharide copolymer comprising the steps or acts of reacting an isocyanate-containing molecule and a poly($C_{2-10}$ alkylene oxide)$_n$ to produce a diisocyanate reactant, and, reacting the diisocyanate reactant with a $C_{4-50}$ diol-containing molecule and the bioactive polysaccharide, whereby n=10 to 40, whereby the $C_{2-10}$ alkylene group in the poly($C_{2-10}$ alkylene oxide), molecule may be linear or branched, substituted or un-substituted, and whereby the $C_{4-50}$ group in the diol-containing molecule may also be linear or branched, substituted or unsubstituted.

In an exemplary embodiment of the method, the bioactive polysaccharide is a bioactive glycosaminoglycan.

In another exemplary embodiment of the method, the bioactive glycosaminoglycan is a suitable salt of hyaluronic acid or a suitable salt of heparin.

In another exemplary embodiment of the method, the suitable salt of hyaluronic acid is a cetylpyridinium salt or a tetrabutylammonium salt, and the suitable salt of heparin is a dimethyldioctadecylammonium salt.

In another exemplary embodiment of the method, the salt of hyaluronic acid has 5 to 10,000 repeating units, and the dimethyldioctadecylammonium salt of heparin has 5 to 65 repeating units.

In another exemplary embodiment of the method, the suitable salt of hyaluronic acid is a cetylpyridinium salt of hyaluronic acid.

In another exemplary embodiment of the method, the weight content of the bioactive polysaccharide, glycosaminoglycan, suitable salt of hyaluronic acid or suitable salt of heparin is in the range of about 0.05% up to about 30%.

In another exemplary embodiment of the method, other endpoints (high or low endpoints) within the range of weight contents of the bioactive polysaccharide, glycosaminoglycan, suitable salt of hyaluronic acid or suitable salt of heparin include about 0.05%, 0.1%, 0.33%, 0.66%, 1.3%, 2.0%, 5.4%, 10%, 20% and 30%.

Another aspect of the invention is a method of making a biocompatible and bioactive polyurethane-butanediol-glycosaminoglycan salt copolymer comprising the steps or acts of reacting 4,4'-methylene-di-(p-phenyl isocyanate) and poly(tetramethylene oxide)$_n$ to produce a diisocyanate reactant, and, reacting the diisocyanate reactant with 1,4-butanediol and a suitable salt of hyaluronic acid or heparin, whereby n=10 to 40.

In another exemplary embodiment of the method, the salt of hyaluronic acid is a cetylpyridinium salt or a tetrabutylammonium salt, and the suitable salt of heparin is a dimethyldioctadecylammonium salt.

In another exemplary embodiment of the method, the salt of hyaluronic acid has 5 to 10,000 repeating units, and the dimethyldioctadecylammonium salt of heparin has 5 to 65 repeating units.

In another exemplary embodiment of the method, the cetylpyridinium salt of hyaluronic acid having 5 to 10,000 repeating units is employed.

In an exemplary embodiment of the method, the weight content of the bioactive glycosaminoglycan salt, salt of hyaluronic acid or salt of heparin is in the range of about 0.05% to about 30%.

In another exemplary embodiment of the method, other endpoints (high or low endpoints) within the range of weight contents of the bioactive glycosaminoglycan salt, salt of hyaluronic acid or salt of heparin include about 0.05%, 0.1%, 0.33%, 0.66%, 1.3%, 2.0%, 5.4%, 10%, 20% and 30%.

Another aspect of the invention is a bioactive and biocompatible polyurethane-butanediol-glycosaminoglycan copolymer for use in medical implant devices. The biocompatible urethane component being the reaction product of 4,4'-methylene-di-(p-phenyl isocyanate) and poly(tetramethylene oxide)$_n$ and further reacted with 1,4-butanediol, wherein n=10 to 40. The bioactive glycosaminoglycan being a salt of hyaluronic acid, such as a cetylpyridinium salt acid having 5 to 10,000 repeating units or a salt of heparin, such as a dimethyldioctadecylammonium salt of heparin has 5 to 65 repeating units. The weight content of the bioactive glycosaminoglycan is an amount sufficient to render the copolymer bioactive. Preferably, the weight content of the polyurethane-diol is an amount sufficient to render the copolymer sufficiently flexible and rigid for endovascular delivery into a vascular aneurysm and for use as a polymeric shell, having coiled NiTi wire disposed therein, within the vascular aneurysm.

DETAILED DESCRIPTION OF THE INVENTION

Hyaluronic acid (also referred to as hyaluronan and hyaluronate) is a suitable molecule for enhancing tissue wound healing response upon in vivo implantation. Hyaluronic acid is a polysaccharide naturally present during wound healing. Hyaluronic acid also facilitates proliferation, migration, and extra-cellular matrix production by various cell types, including vascular endothelial and smooth muscle cells. (Leach J B et al., *Encyclopedia of Biomaterials and Biomedical Engineering* Wnek G E et al., Eds. (Marcel Dekker, New York, 2004) pp. 779-789).

Advantageously, hyaluronic acid has low immunogenicity and non-thrombogenic properties as distinguished from other molecules that induce wound healing. For example, collagen is highly thrombogenic and unsuitable for intravascular use.

Hyaluronic acid is a member of the polysaccharide family of compounds, specifically the GAG family. GAGs (also referred to as mucopolysaccharides) are long unbranched polysaccharides having repeating disaccharide units, which contains an N-acetyl-hexosamine and hexose (or hexuronic acid). The combination of the sulfate group and the carboxylate groups of the uronic acid residue provides a high negative density charge. Members of the GAG family of compounds include hyaluronic acid, heparin, dermatan sulfate, chondroitin sulfate and others. Heparin is generally described in Linhardt R J et al., "Isolation and characterization of human heparin," *Biochemistry* 1992, 31(49): 12441-12445.

Polyurethane (PU) polymers are characterized by a chain of organic units joined by urethane linkages. Polyurethanes are commonly made by reacting a diisocyanate (aromatic or aliphatic) and a polyol (such as a polyether polyol, like polyethylene glycol, or a polyester polyol). An exemplary polyol is 1,4-butanediol. An exemplary diisocyanate is the reaction product of 4,4'-methylene-di(p-phenyl isocyanate) and poly (tetramethylene oxide)n, whereby n=10 to 40.

Polyurethane may be fabricated using a wide variety of processing technologies, such as casting, electrostatic and wet fiber/monofilament spinning, extrusion, dip coating, and spraying.

An exemplary embodiment of the invention is directed to a bioactive and biocompatible PU-diol-GAG salt copolymers, specifically polyurethane-butanediol-hyaluronic acid salt (PUBD-HA) copolymers, for use in medical implant devices. The biocompatible urethane component being the reaction product of 4,4'-methylene-di-(p-phenyl isocyanate) and poly (tetramethylene oxide)11 and further reacted with 1,4-butanediol, wherein n=10 to 40.

In another exemplary embodiment, the bioactive GAG is a salt of hyaluronic acid, such as a cetylpyridinium salt acid having 5 to 10,000 repeating units or a dimethyldioctadecylammonium salt of heparin has 5 to 65 repeating units. The weight content of GAG (i.e., the cetylpyridinium salt or the dimethyldioctadecylammonium salt) is an amount sufficient to render the copolymer bioactive. Preferably, the weight content of the polyurethane-diol is an amount sufficient to render the copolymer sufficiently flexible and rigid for endovascular delivery into a vascular aneurysm and for use as a polymeric shell, having coiled NiTi wire disposed therein, within the vascular aneurysm.

In general, preferred uses of the invention is synthesis of an elastic, compliant polymer shell that induces suitable wound healing responses, such as the bioactive spherical aneurysm occlusion device shown in the related patent application set forth herein. Preferably, the polymer shell is also hemocompatible. The polymer combines the elasticity and mechanical strength of polyurethane with the bioactivity of hyaluronic acid.

Example 1

As shown in FIG. 5, a polyurethane prepolymer is synthesized and reacted with the cetylpyridinium salt of hyaluronic acid to make the PUBD-HA copolymer. Thin, transparent films of PUBD are synthesized by solvent casting, whereby the films possess excellent mechanical strength (5.3-11 MPa elastic modulus) and elasticity (>1000% elongation). The biocompatibility and bioactivity of PUBD-HA is confirmed using in vitro cell culture tests. Endothelial cells and fibroblasts are cultured upon PUBD-HA or PUBD for time periods up to 5 days. Using conventional assays, the cultures are used to assess cell viability and number.

Hyaluronic Acid Degradation. Native hyaluronic acid has a very high molecular weight (~4 MDa). Hyaluronic acid that is lower in molecular weight is easier to handle (with respect to dissolution), and it stimulates endothelialization and wound healing. The following steps were taken to partially degrade hyaluronic acid creating low molecular weight hyaluronic acid, which is easier to use in chemical synthesis.

Starting materials include hyaluronic acid sodium salt having MW=4 MDa (Fluka) and hyaluronidase (from bovine testes, 1040 U/ml, Sigma) were procured.

Methods. A 5 mg/ml solution of hyaluronic acid in 20 ml diH$_2$O was prepared in a 50 ml centrifuge tube. Hyaluronidase (HyAse) was added to the hyaluronic acid-containing aqueous solution producing a HyAse concentration of 500 U/ml. The solution was incubated in a 37° C. water bath overnight, and then it was heated in a 70° C. water bath for 30 minutes to inactivate the HyAse. After cooling to room temperature, 2 ml of the degraded hyaluronic acid solution was transferred to a 15 ml centrifuge tube for ion exchange with cetylpyridinium chloride (CPC). The degraded hyaluronic had MW=9300. Degraded HA was also purchased from Lifecore Biomedical, Inc.

Synthesis of HA-CPC. Hyaluronic acid and the degradation products are soluble in H$_2$O. Synthesis of polyurethane-hyaluronic acid copolymers (PU-HA) involves dissolving hyaluronic acid in organic solvent(s) such as dimethyl formamide (DMF) or tetrahydrofuran (THF). The following method describes a simple ion exchange reaction that replaces the sodium salt of hyaluronic acid with a cetylpyridinium salt of hyaluronic acid, whereby the latter is soluble in DMF.

Starting materials include un-degraded and degraded hyaluronic acid (of any molecular weight), cetylpyridinium chloride (Sigma) and anhydrous N,N-dimethylformamide (DMF)(Aldrich).

Methods. A 0.48% (w/v) solution of CPC in 2 ml diH$_2$O was added dropwise to 2 ml of hyaluronic acid solution forming a white precipitate. The precipitate was separated from the solution by centrifugation. After removing the supernatant, the precipitate was washed using 2 ml diH$_2$O and centrifuged, whereby the supernatant was removed again. The precipitate was frozen and dried overnight. The end-product was HA-CPC powder having approximately 25 HA repeating units.

Synthesis of PUBD-HA. Synthesizing a copolymer of polyurethanebutanediol and hyaluronic acid. Starting materials include methylene di(p-phenyl isocyanate) (MDI)(Aldrich), poly(tetramethylene oxide) (PTMO) having n=14 and Mn=1000 (Aldrich), 1,4-butanediol (BD), anhydrous N,N-dimethylformamide (DMF)(Aldrich), and HA-CPC powder.

Methods. A 10% (w/v) solution of MDI (2 mmol; MW=250) in 5 ml of DMF was prepared in a 100 ml round-bottom flask and stirred at room temperature. A 10% (w/v) solution of PTMO (1 mmol; MW=1000) in 10 ml of anhydrous DMF was added. The mixture was heated to 90° C. and maintained at that temperature for 3 h under argon. The reactor was cooled to room temperature. BD (0.9 mmol; MW=90) in 2 mL of anhydrous DMF was added. The HA-CPC powder was dissolved in 4 ml anhydrous DMF and warmed to 50° C. The HA-CPC solution in DMF was added to the reactor and incubated at 50° C. for 3 h under argon. The polymer solution was cooled to room temperature, precipitated in methanol, and dried naturally in a hood. The end-product was the copolymer PUBD-HA shown in FIG. 5.

Five PUBD-HA copolymers were synthesized, whereby the weight % content of hyaluronic acid was 0.33%, 0.66%, 1.33%, 2% and 5.4%. The content of each copolymer was verified using 1H NMR for incorporation of hyaluronic acid into the polyurethane backbone.

Films of PUBD-HA were created by dissolving suitable amounts of copolymer with DMF in a Teflon evaporation dish. The solvent was allowed to evaporate leaving polymer films of ~200 µm thickness. These films can be sterilized using ethanol, UV exposure, or EtO treatment.

The instant compositions are not enzymatically degradable by hyaluronidase. Theoretically, at elevated hyaluronic acid content levels, the PUBD-HA copolymers may become enzymatically degradable.

Results and Contact Angle. The contact angle of $diH_2O$ on a copolymer film decreased with increasing hyaluronic acid content ($p<0.01$ by one-way ANOVA), which indicates increased hydrophilicity with increased hyaluronic acid content. *$p<0.03$ compared to PUBD by two-tailed t-test.

Mechanical Properties. With the exception of copolymer containing 0.33% hyaluronic acid, no significant change was observed in tensile strength. Elastic modulus significantly increased with increasing hyaluronic acid content ($p<0.001$ by one-way ANOVA). *$p<0.001$ compared to PUBD by two-tailed t-test.

Fibroblast Adhesion and Proliferation. Increased hyaluronic acid content resulted in decreased adhesion. It also resulted in decreased proliferation of NIH 3T3 fibroblasts cultured on PUBD-HA films ($p<0.001$ by one-way ANOVA for both time points), which may change depending upon molecular weight of hyaluronic acid and cell type. The PUBD-HA copolymer may inherently inhibit cell adhesion and proliferation. The MW of the tested hyaluronic acid inhibited the proliferation of fibroblasts. Other experiments will determine whether endothelial cells behave in a similar manner.

Haemocompatibility

Figure 11:
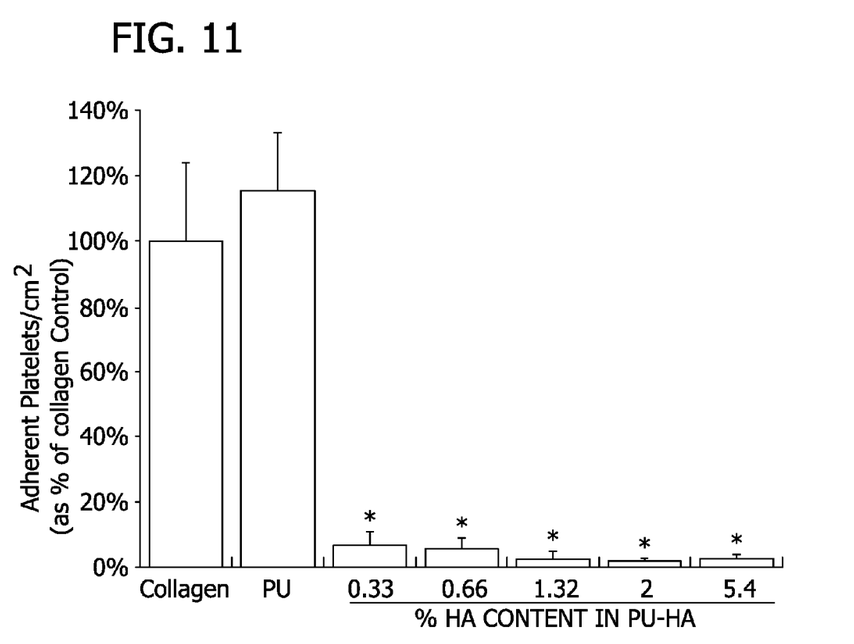
FIG. 11 shows platelet adhesion to PU-HA copolymers.

Static platelet adhesion was studied for all the polymer films. Collagen-coated glass coverslips, which are naturally thrombogenic surfaces, were used as the positive control. The results show platelet adhesion was significantly inhibited by the PU-HA copolymers. The inclusion of HA in the PU polymer proved to be highly effective in creating haemocompatible films. Results are illustrated in FIG. 11.

Example 2

Starting materials include heparin sodium salt having MW=16,000 (Sigma).

Synthesis of Hep-DDA. Heparin is soluble in $H_2O$. Synthesis of polyurethane-heparin copolymers (PU-Hep) involves dissolving heparin in organic solvent(s) such as dimethyl formamide (DMF) or tetrahydrofuran (THF). The following method describes a simple ion exchange reaction that replaces the sodium salt of heparin with a dimethyldioctadecylammonium salt of heparin, whereby the latter is soluble in DMF.

Starting materials include un-degraded and degraded heparin (of any molecular weight), dimethyldioctadecylammonium chloride (DDAC) (Fluka) and anhydrous N,N-dimethylformamide (DMF)(Aldrich).

Methods. A 0.48% (w/v) solution of DDAC in 2 ml $diH_2O$ was added dropwise to 2 ml of sodium heparin solution, forming a white precipitate. The precipitate was separated from the solution by centrifugation. After removing the supernatant, the precipitate was washed using 2 ml $diH_2O$ and centrifuged, whereby the supernatant was removed again. The precipitate was frozen and dried overnight. The end-product was Hep-DDA powder having approximately 27 Hep repeating units.

Synthesis of PUBD-Hep. Synthesizing a copolymer of polyurethanebutanediol and heparin. Starting materials include methylene di(p-phenyl isocyanate) (MDI) (Aldrich), poly(tetramethylene oxide) (PTMO) having n=14 and Mn=1000 (Aldrich), 1,4-butanediol (BD), anhydrous N,N-dimethylformamide (DMF) (Aldrich), and Hep-DDA powder.

Methods. A 10% (w/v) solution of MDI (2 mmol; MW=250) in 5 ml of DMF was prepared in a 100 ml round-bottom flask and stirred at room temperature. A 10% (w/v) solution of PTMO (1 mmol; MW=1000) in 10 ml of anhydrous DMF was added. The mixture was heated to 90° C. and maintained at that temperature for 3 h under argon. The reactor was cooled to room temperature. BD (0.9 mmol; MW=90) in 2 mL of anhydrous DMF was added. The Hep-DDA powder was dissolved in 4 ml anhydrous DMF and warmed to 50° C. The Hep-DDA solution in DMF was added to the reactor and incubated at 50° C. for 3 h under argon. The polymer solution was cooled to room temperature, precipitated in methanol, and dried naturally in a hood. The end-product was the copolymer PUBD-Hep shown in FIG. 6.

Two PUBD-Hep copolymers were synthesized, whereby the weight % content of heparin was 0.66% and 1.33%.

Films of PUBD-Hep were created by dissolving suitable amounts of copolymer with DMF in a Teflon evaporation dish. The solvent was allowed to evaporate leaving polymer films of ~200 µm thickness. These films can be sterilized using ethanol, UV exposure, or EtO treatment.

Example 3

Formation of Dodecyltrimethylammonium Salt of Dermatan Sulfate

A 50 mg/ml solution of dermatan sulfate (DS) in 20 ml $diH_2O$ was prepared in a 50 ml centrifuge tube and 0.4 ml of this DS solution was transferred to a 15 ml centrifuge tube. A 100 mg/ml solution of dodecyltrimethylammonium chloride (DTAC) in 0.21 ml $diH_2O$ was added dropwise to the 0.4 ml of DS solution, leading to formation of a white precipitate (DS-DTA). The precipitate was separated from the solution by centrifugation and washed twice with $diH_2O$. The precipitate was frozen and dried overnight. The product was DS-DTA powder, which is soluble in N,N-dimethylformamide (DMF). Unless otherwise noted, all chemicals were obtained from Sigma-Aldrich (St. Louis, Mo.).

Synthesis of Polyurethane-Dermatan Sulfate (PU-DS) Polymers

A 10% (w/v) solution of methylene di(p-phenyl isocyanate) (MDI; 4 mmol; MW=250) in 10 ml of anhydrous DMF was prepared in a 100 ml round-bottom flask and stirred at room temperature. A 10% (w/v) solution of poly(tetramethylene oxide) (PTMO; 2 mmol; MW=1000) in 20 ml of anhydrous DMF was added, and the mixture was heated to 90° C. and held there for 3 h under argon. The reactor was cooled to room temperature before 1,4-butanediol (BD; 1.8 mmol; MW=90) in 2 ml of anhydrous DMF was added. The DS-DTA powder was dissolved in 4 ml anhydrous DMF and warmed to 50° C. The DS-DTA solution in DMF was then added to the reactor and incubated at 50° C. for 20 h under argon. The polymer solution was cooled to room temperature, precipitated in methanol, and dried naturally in a fume hood. This product is referred to as PU-DS in this study. The weight percent of DS in the copolymer was varied by incorporating different amounts of DS-DTA into the synthesis. The reaction time of the second step of the PU-DS synthesis was increased to 20 hours, compared to 3 hours for PU, because the prepolymer needs a longer time to encounter the bulkier DS molecule. The resulting PU-DS copolymers, with DS content ranging from 0.6-10%, were characterized via $^1$H NMR.

Formation of PU-DS Films

Figure 7:
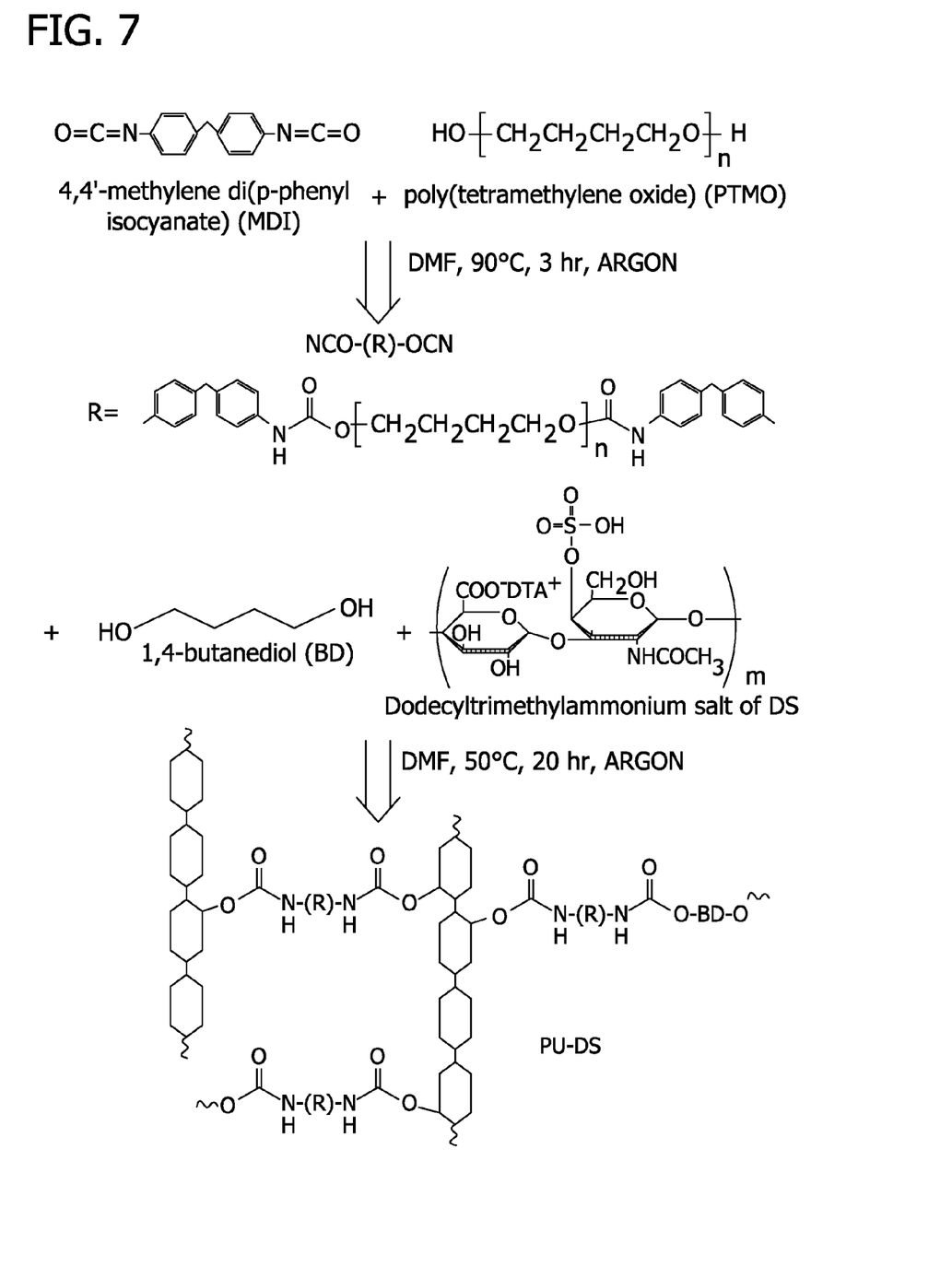
FIG. 7 is a schematic illustration of the synthesis of PU and PU-DS copolymers as described in Example 3.
Figure 8A:
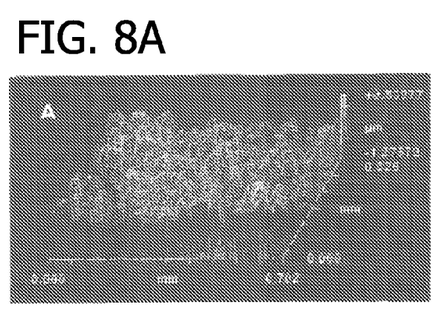
FIG. 8 shows topographical photomicrographs of various films described in Example 3.
Figure 8B:
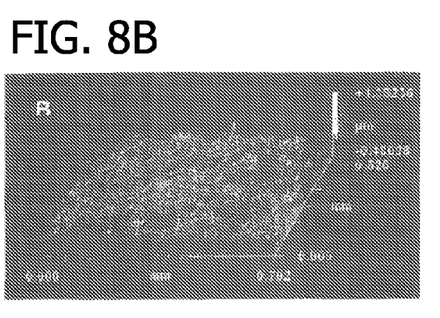
Figure 8C:
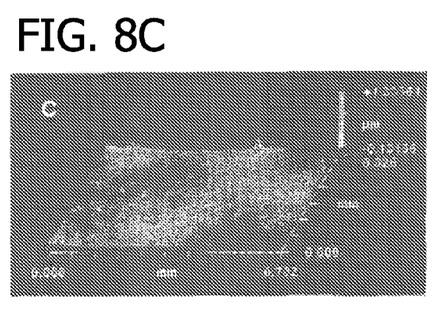
Figure 8D:
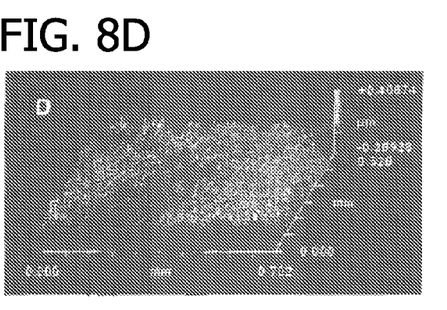
Figure 8E:
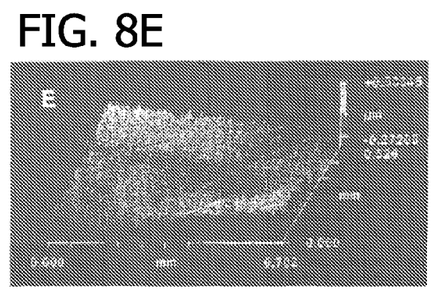
Figure 8F:
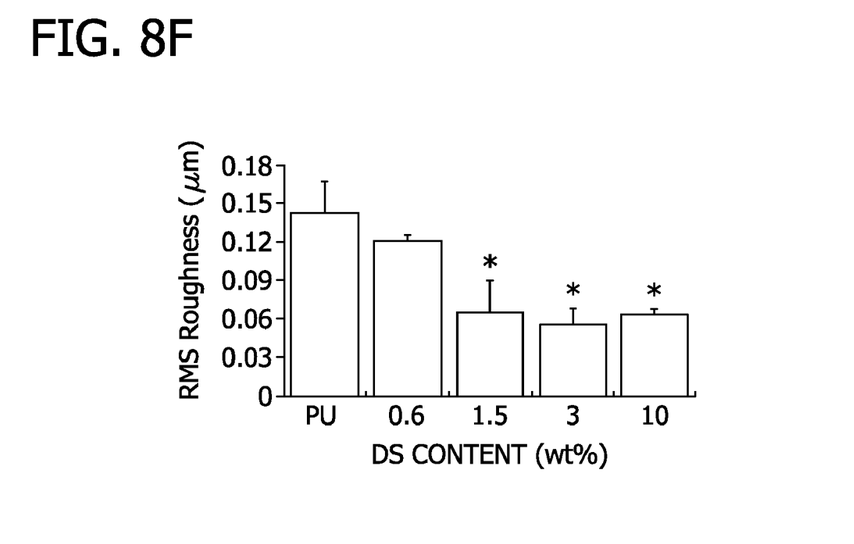

Films of PU-DS were created by pipetting 0.1 ml of a 20 mg/ml polymer solution in DMF onto 12 mm diameter glass coverslips, and allowing the solvent to evaporate, leaving polymer films of ~20 μm thickness. The films were used for all contact angle, topography, biocompatibility and haemocompatibility studies. A schematic illustration of the synthesis of PU and PU-DS copolymers is shown in FIG. 7.

Contact Angle and Surface Energy

Contact angles for three liquids—deionized water, ethylene glycol, and glycerol—were obtained using a standard automated goniometer (Model 200, Rame-Hart Inc., Netcong, N.J.). A 20 μl droplet of test liquid was placed on a flat horizontal polymer film surface, and the angle between the baseline of the drop and the tangent at the drop boundary was measured by a CCD camera linked to the manufacturer's contact angle software (DROPimage CA Standard). For each liquid, readings for every angle measurement were taken five times, and three samples were measured for each polymer film. Each measurement for all experiments was performed at a consistent time point after the liquid was dropped on the surface to eliminate variability introduced by evaporation.

Topography and Roughness

Surface topography and roughness of PU and PU-DS films were evaluated using a scanning white light interferometer (Zygo NewView 6300 Optical Profiler, Zygo Corp., Middlefield, Conn.). Polymer samples were cast on glass coverslips as described in film-casting section, and then analyzed by the interferometer using a 10× interferometric objective, 1× field zoom lens, 20 μm scan length, and <0.1 nm vertical resolution. Captured images were analyzed using Metropro™ 8.1.5 software to obtain values for RMS roughness in five 0.7 mm×0.5 mm areas per sample film. RMS roughness is defined as the root mean squared value of all vertical deviations from the mean surface level.

Cell Culture and Maintenance

Fibroblasts (NIH 3T3s, ATCC, Manassas, Va.) were cultured in normal growth medium (DMEM supplemented with 10% FBS, 100 units/ml penicillin, 100 μg/ml streptomycin and 2 mM L-Glutamine) at 37° C., 5% $CO_2$. An immortalized human macrophage cell line (U932s) was cultured.

Biocompatibility

PU and PU-DS films were sterilized via immersion in 70% ethanol, allowed to dry, and then seeded with 3T3 fibroblasts at a density of $20 \times 10^3$ cells/cm$^2$. At five hours and five days post-seeding, cells were lysed in M-PER buffer (M-PER Mammalian Protein Extraction Reagent, Pierce, Rockford, Ill.), and a dsDNA assay (Quant-iT™ Pico Green® dsDNA Assay Kit, Invitrogen, Carlsbad, Calif.) was performed upon the lysate in order to quantify cell adhesion at t=5 hours and cell proliferation at t=5 days.

Mechanical Testing

To create thicker polymer samples for use in mechanical testing studies, sheets of PU and PU-DS (60-130 μm thickness) were cast by pipetting 4 ml of a 75 mg/ml copolymer solution into 63 mm diameter Teflon evaporation dishes and allowing the solvent to evaporate. Polymer films were then sandwiched between pieces of waxed weigh paper and cut into a dogbone geometry (a scaled variant of the ASTM D638-03 type V specimen with a 4 mm gage length, 1.7 mm gage width, and 1 mm fillet radii) using a steel template and razor blade. The smaller fillet radii created a smaller transition region, allowing for a more clearly defined gage section, however, the fillet radii were large enough such that rupture from stress concentrations in the transition region did not occur. The thickness of each polymer sample was determined through optical microscopy.

Tensile testing was performed using an Instron 5548 MicroTester equipped with a 10 N load cell. Crosshead displacement was used to determine axial strain in the gage section. Custom-made tensile grips, which utilize self-aligning faces and screw tightening mechanisms, held the samples during testing with the assistance of fine grit sandpaper adhered to the grip faces to prevent slip. All samples were loaded to rupture. A constant crosshead displacement rate of 25 mm/min was used for all tests because it produced rupture in the gage section within the 0.5 to 5 minute suggested timeframe of ASTM D638-03. Displacement and load data were gathered from which stress-strain curves were obtained, using the initial cross sectional area of the gage section and the initial 4 mm gage length.

Young's modulus, E, was obtained by calculating the slope of the initial linear region of the stress-strain curve. Ultimate tensile strength (the maximum stress achieved prior to rupture) and percent elongation at break (the strain at rupture) were also obtained from the stress-strain curves.

Haemocompatibility

For the Examples herein, static platelet adhesion was measured on collagen-coated coverslips and films made of PU and PU-DS (or other films). Glass coverslips (12 mm diameter) were coated for 1 h at 37° C. in 0.6 mg/ml collagen type I (Angiotech Pharmaceuticals, Inc., Vancouver, Canada) as a positive control, while PU and PU-DS films were prepared as described earlier. Whole blood was obtained via venipuncture from a healthy volunteer and collected in Vacutainers® pre-loaded with acid-citrate-dextrose solution (BD Diagnostics, Franklin Lakes, N.J.). The polymer and control substrates were incubated with the whole blood for 30 minutes at 37° C., followed by five rinses in PBS and fixation in 2.5% glutaraldehyde solution. Photomicrographs of four randomly-chosen fields of view for each of three samples per condition were captured (200× magnification), and the number of platelets adherent to the substrate in each field of view were counted manually.

Results and Discussion

The approximate yield of the PU-DS product for all formulations was 80% compared to the maximum theoretical yield. All copolymers were solvent-cast into thin films for surface characterization, biocompatible characterization and haemocompatibility analysis. The thin films were transparent and approximately 90-120 μm in thickness.

Contact Angle and Surface Energy

The contact angle and surface energy results for PU-DS copolymer formulations are summarized in Table 1. As expected, the contact angle of water on copolymer films decreased with increasing DS content, indicating higher hydrophilicity. The two PU-DS films with the highest hydrophilicity had uneven droplet shapes nearing complete surface wetting, and therefore could not be measured with the goniometer.

TABLE 1

Contact angle and surface energy values for PU and PU-DS films.

| Material | Contact Angle | | | Surface Energy Parameters | | | Surface Energy (mJ/m$^2$) |
|---|---|---|---|---|---|---|---|
| | Water | Glycerol | Ethylene Glycol | $\gamma^d$ | $\gamma^-$ | $\gamma^+$ | |
| PU | 79.81 | 72.91 | 58.99 | 2.89 | 3.48 | 2.33 | 24.57 ± 0.61 |
| PU-DS 0.6% | 78.82 | 73.53 | 59.85 | 3.29 | 3.621 | 1.94 | 24.89 ± 0.29 |
| PU-DS 1.5% | 77.15 | 73.92 | 60.61 | 3.51 | 3.89 | 1.68 | 25.35 ± 0.64 |
| PU-DS 3% | ~0* | 82.57 | 63.39 | / | / | / | / |
| PU-DS 5.4% | ~0* | 79.45 | ~0* | / | / | / | / |

*Surfaces were immediately fully wetted by the test liquid, with no measurable contact angle.

Topography and Roughness

Topography of films for PU and PU-DS was analyzed using an interferometer, and the photomicrographs are shown in FIG. 8. The topographical features were similar for all PU and PU-DS polymers with the exception of PU-DS 1.5%. In general, the films became less rough with increased DS content in the copolymers, as demonstrated by FIG. 8F.

Cytocompatibility

Figure 9:
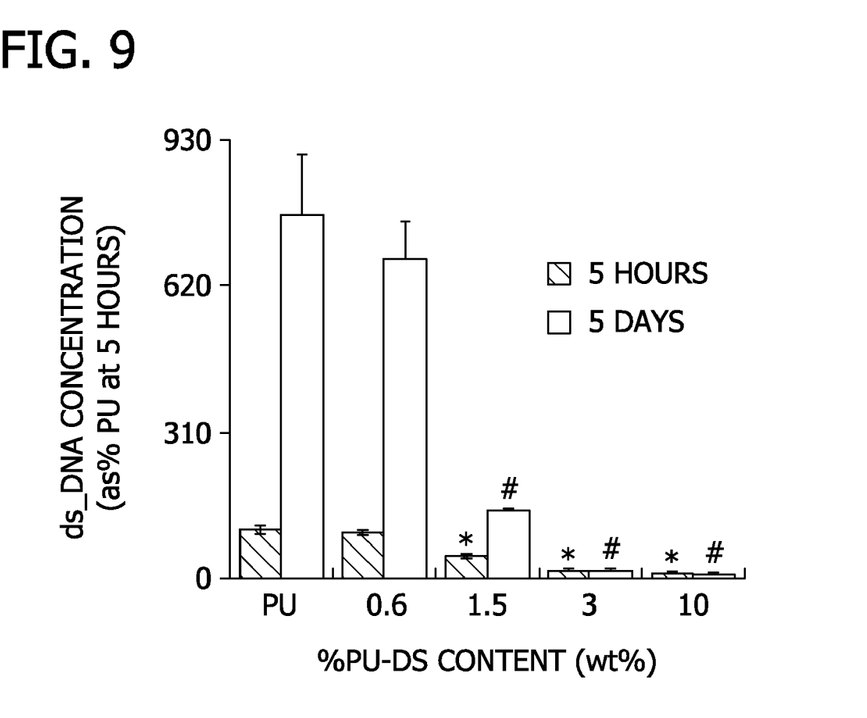
FIG. 9 shows fibroblast adhesion to the films described in Example 3.
Figure 10A:
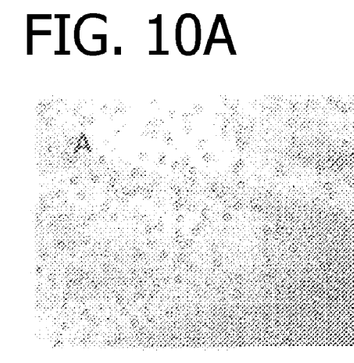
FIG. 10 shows red blood cell and platelet adhesion to PU-DS copolymers.
Figure 10B:
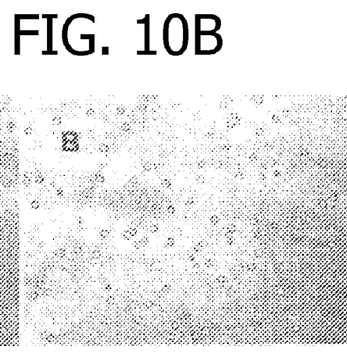
Figure 10C:
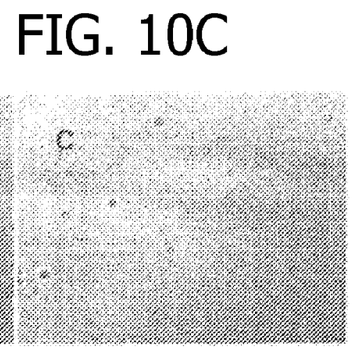
Figure 10D:
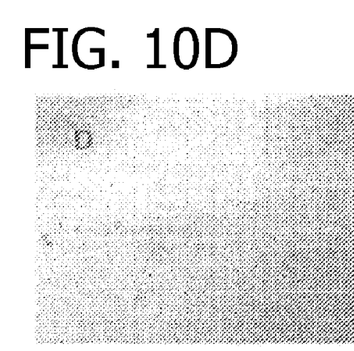
Figure 10E:
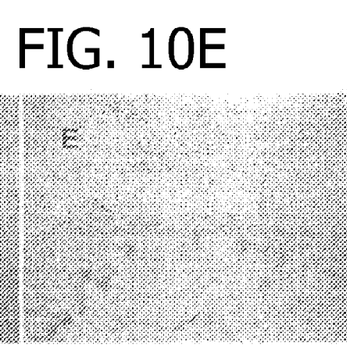
Figure 10F:
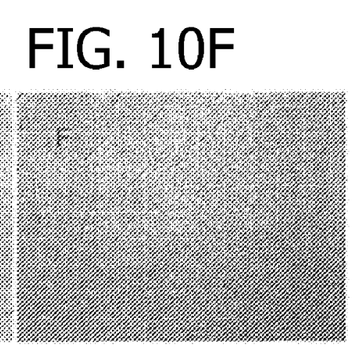
Figure 10G:
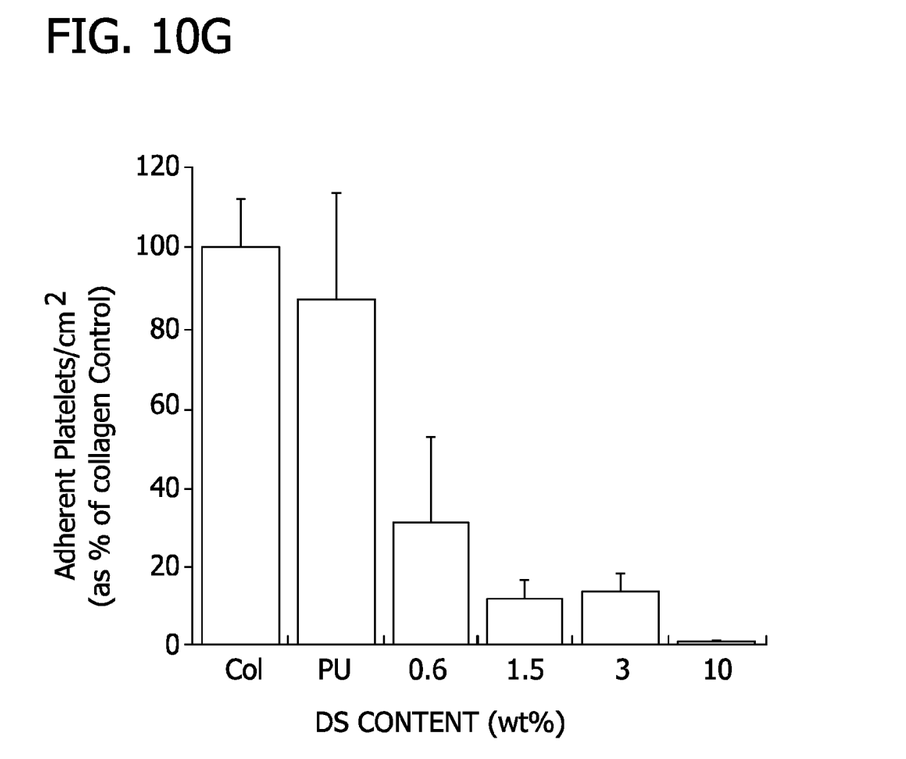

The results in shown in FIG. 9 show that fibroblast seeding on PU-DS 0.6% resulted in a similar level of cell adhesion as the PU alone at 5 hours post-seeding. The PU-DS films with higher than 0.6 wt % DS were significantly less supportive of cell adhesion compared to PU (p<0.03), with almost negligible cell adhesion on PU-DS 3% and 10%. Meanwhile, fibroblast proliferation on PU-DS 0.6% was not different from the PU control, but films with greater DS content did not support the proliferation of fibroblasts. For higher DS concentrations (3% and 10%), the number of adherent fibroblasts at 5 days remained negligible, highlighting the strong anti-cell-adhesive behavior of these materials.

Haemocompatibility

Static platelet adhesion was studied for all the polymer films. Collagen-coated glass coverslips, which are naturally thrombogenic surfaces, were used as the positive control. The results show that both red blood cell and platelet adhesion were significantly inhibited by the PU-DS copolymers. Platelet adhesion was decreased by 3-fold on the lowest DS concentration, and a negligible number of platelets were found on the 10 wt % PU-DS. The inclusion of DS in the PU polymer proved to be highly effective in creating haemocompatible films. Results are illustrated in FIG. 10.

We claim:

1. A copolymer comprising the polymerization reaction product of a biocompatible polyurethane and a bioactive polysaccharide, wherein the bioactive polysaccharide is incorporated into the polyurethane backbone of the copolymer.

2. The copolymer of claim 1, wherein the bioactive polysaccharide is a bioactive glycosaminoglycan.

3. The copolymer of claim 2, wherein the bioactive glycosaminoglycan is a member selected from the group consisting of a suitable salt of hyaluronic acid, a suitable salt of heparin, and a suitable salt of dermatan sulfate.

4. The copolymer of claim 3, wherein the salt of hyaluronic acid is a member selected from the group consisting of a cetylpyridinium salt and a tetrabutylammonium salt, and wherein the salt of heparin is a dimethyldioctadecylammonium salt.

5. The copolymer of claim 4, wherein the salt of hyaluronic acid has 5 to 10,000 repeating units, and wherein the dimethyldioctadecylammonium salt of heparin has 5 to 65 repeating units.

6. The copolymer of claim 1, wherein the weight content of the bioactive polysaccharide is in the range of about 0.05% to about 30%.

7. The copolymer of claim 6, wherein the high and low range endpoints of the weight content of the bioactive polysaccharide are any combination of members selected from the group consisting of 0.05%, 0.1%, 0.33%, 0.66%, 1.3%, 2.0%, 5.4%, 10%, 20% and 30%.

8. The copolymer of claim 7, comprising the cetylpyridinium salt of hyaluronic acid.

9. The copolymer of claim 7, wherein the biocompatible polyurethane is the reaction product of 4,4'-methylene-di-(p-phenyl isocyanate) and poly(tetramethylene oxide)$_n$ and further reacted with 1,4-butanediol, and wherein n=10 to 40.

10. The copolymer of claim 8, wherein the biocompatible polyurethane is the reaction product of 4,4'-methylene-di-(p-phenyl isocyanate) and poly(tetramethylene oxide)$_n$ and further reacted with 1,4-butanediol, and wherein n=10 to 40.

11. The copolymer of claim 6, wherein the biocompatible polyurethane is the reaction product of a suitable isocyanate-containing molecule and a suitable poly($C_{2-10}$ alkylene oxide)$_n$ and further reacted with a suitable $C_{4-50}$ diol-containing molecule, wherein n=10 to 40, wherein the $C_{2-10}$ alkylene is linear or branched, substituted or un-substituted, and wherein the $C_{4-50}$ is linear or branched, substituted or un-substituted.

12. A method of making a bioactive and biocompatible polyurethane-diol-polysaccharide copolymer comprising:
   reacting a suitable isocyanate-containing molecule and a suitable poly($C_{2-10}$ alkylene oxide)$_n$ to produce a diisocyanate reactant, and, reacting the diisocyanate reactant with a suitable $C_{4-50}$ diol-containing molecule and a bioactive polysaccharide,
   wherein n=10 to 40,
   wherein the $C_{2-10}$ alkylene is linear or branched, substituted or un-substituted, and,
   wherein the $C_{4-50}$ is linear or branched, substituted or un-substituted.

13. The method of claim 12, wherein the bioactive polysaccharide is a bioactive glycosaminoglycan.

14. The method of claim 13, wherein the glycosaminoglycan is a member selected from the group consisting of a suitable salt of hyaluronic acid, a suitable salt of heparin, and a suitable salt of dermatan sulfate.

15. The method of claim 14, wherein the salt of hyaluronic acid is a member selected from the group consisting of a cetylpyridinium salt and a tetrabutylammonium salt, and wherein the salt of heparin is a dimethyldioctadecylammonium salt.

16. The method of claim 15, wherein the salt of hyaluronic acid has 5 to 10,000 repeating units, and wherein the dimethyldioctadecylammonium salt of heparin has 5 to 65 repeating units.

17. The method of claim 12, wherein the weight content of the bioactive polysaccharide is in the range of about 0.05% to about 30%.

18. The method of claim 17, wherein the high and low range endpoints of the weight content of the bioactive polysaccharide are any combination of members selected from the group consisting of 0.05%, 0.1%, 0.33%, 0.66%, 1.3%, 2.0%, 5.4%, 10%, 20% and 30%.

19. A method of making a bioactive and biocompatible polyurethane-butanediol-glycosaminoglycan salt copolymer comprising:
  reacting 4,4'-methylene-di-(p-phenyl isocyanate) and poly(tetramethylene oxide)$_n$ to produce a diisocyanate reactant, and,
  reacting the diisocyanate reactant with 1,4-butanediol and a bioactive glycosaminoglycan salt selected from the group consisting of a suitable salt of hyaluronic acid and a suitable salt of heparin,
  wherein n=10 to 40.

20. The method of claim 19, wherein the salt of hyaluronic acid is a member selected from the group consisting of a cetylpyridinium salt and a tetrabutylammonium salt, and wherein the salt of heparin is a dimethyldioctadecylammonium salt.

21. The method of claim 20, wherein the salt of hyaluronic acid has 5 to 10,000 repeating units, and wherein the dimethyldioctadecylammonium salt of heparin has 5 to 65 repeating units.

22. The method of claim 21, comprising the cetylpyridinium salt of hyaluronic acid having 5 to 10,000 repeating units.

23. The method of claim 19, wherein the weight content of the bioactive glycosaminoglycan salt is in the range of about 0.05% to about 30%.

24. The method of claim 23, wherein the high and low range endpoints of the weight content of the bioactive glycosaminoglycan salt are any combination of members selected from the group consisting of 0.05%, 0.1%, 0.33%, 0.66%, 1.3%, 2.0%, 5.4%, 10%, 20% and 30%.

* * * * *